United States Patent
Schlieper et al.

[11] Patent Number: 5,891,687
[45] Date of Patent: Apr. 6, 1999

[54] POSITIVE SELECTION VECTOR BASED ON THE CAPS GENE, PCAPS VECTOR AND ITS USE

[75] Inventors: Daniel Schlieper, Köln; Harlad Sobek; Manfred Schmidt, both of Penzberg; Brigitte von Wilcken-Bergmann, Köln; Benno Müller-Hill, Köln, all of Germany

[73] Assignee: Boehringer Mannheim GmbH, Mannheim, Germany

[21] Appl. No.: 892,272

[22] Filed: Jul. 14, 1997

[30] Foreign Application Priority Data

Jul. 29, 1996 [DE] Germany .................. 196 30 617.5

[51] Int. Cl.⁶ .............................. C12N 15/00; C12P 19/34
[52] U.S. Cl. .................. 935/172.3; 435/91.4; 435/91.41; 435/252.3; 435/252.33; 435/320.1; 536/23.1; 536/24.1; 536/24.2
[58] Field of Search ............................ 435/320.1, 252.33, 435/91.1, 172.3, 252.3, 91.4, 91.41; 536/23.1, 24.1, 24.2

[56] References Cited

PUBLICATIONS

Ebright et al., Mutation that alter the DNA sequence specificity of the catabolite gene activator protein of E. coli, Nature v. 311, 232 (Sep. 26, 1984).

Henrich et al., Positive–selection vector with enhanced lytic potential based on a variant of phi X174 phage gene E, Gene v. 154, 51–54 (Mar. 2, 1995).

Primary Examiner—John L. LeGuyader
Attorney, Agent, or Firm—Nikaido Marmelstein Murray & Oram LLP

[57] ABSTRACT

A vector according to the invention with a positive selection possibility for cloning a DNA sequence into a host cell transformed with the vector, wherein the vector contains suitable restriction cleavage sites within a selection gene the functional expression of which is prevented by insertion of the foreign gene is characterized in that it contains a modified cap gene as the selection gene which codes for a CAP protein with modified DNA binding specificity the expression of which is lethal for adenylate-cyclase-positive host cells.

10 Claims, 4 Drawing Sheets

```
                                          GGTACCCTCGAGATAAAAAATTTATTTGCT
TTCAGGTACAATTCTTGATATAATTATCATCTAGATAAATAAAAATTTAAGGATCTT
 M   V   L   G   K   P   Q   T   D   P   T   L   E   W   F
ATG GTA CTT GGT AAA CCT CAA ACG GAT CCT ACT CTC GAA TGG TTC
                                BamHI
 L   S   H   C   H   I   H   K   Y   P   S   K   S   T   L
TTG TCT CAT TGC CAC ATT CAT AAG TAC CCA TCC AAG AGC ACG CTT
 I   H   Q   G   E   K   A   E   T   L   Y   Y   I   V   K
ATT CAC CAG GGT GAA AAA GCG GAA ACG CTG TAC TAC ATC GTT AAA
 G   S   V   A   V   L   I   K   D   E   E   G   K   E   M
GGC TCT GTG GCA GTG CTG ATC AAA GAC GAA GAG GGT AAA GAA ATG
                        BclI
 I   S   Y   L   N   Q   G   D   F   I   G   E   L   G
ATC CTC TCC TAT CTG AAT CAG GGT GAT TTT ATT GGC GAA CTG GGC
 L   F   E   E   G   Q   S   R   S   A   W   V   R   A   K
CTG TTT GAA GAG GGC CAG AGC CGT AGC GCA TGG GTA CGT GCG AAA
 T   A   C   E   V   A   E   I   S   Y   K   F   R   Q
ACC GCC TGT GAA GTG GCT GAA ATT TCG TAC AAA TTT CGC CAA
```

| FIG.1a | FIG.1b |

FIG.1b

```
 L   I   Q   V   N   P   D   I   L   M   R   L   S   A   Q
TTG ATT CAG GTA AAC CCG GAC ATT CTG ATG CGT TTG TCT GCA CAG

M   A   R   R   L   D   V   L   Q   S   S   G   R   I   A   Q   L   N
ATG GCG CGT CGT CTG GAC GTG CTG CAA AGC GGC CGC ATT GCA CAG CTG AAT
                                        NotI

A   F   L   D   V   Q   S   S   G   R   I   A
GCG TTC CTC GAC GTG AGC GGC

L   A   K   Q   P   D   A   M   T   H   P   D   G   M   Q
CTG GCA AAA CAA CCA GAC GCT ATG ACT CAC CCG GAC GGT ATG CAA
                              BalI

I   K   I   T   R   Q   E   I   G   Q   I   V   G   C   S
ATC AAA ATT ACC CGT CAG GAA ATT GGC CAG ATT GTC GGC TGC AGT
                                                        PstI

R   Q   T   V   G   R   I   L   K   M   L   E   D   Q   N
CGT CAA ACC GTG GGA CGC ATA CTT AAG ATG CTC GAG GAT CAG AAC
                                  AflII       XhoI

L   I   S   A   H   G   K   T   I   V   V   Y   G   T   R
CTG ATC TCC GCA CAC GGT AAA ACC ATC GTC GTT TAC GGC ACT CGT
  *
TAA TCCCGTCGGAGTGGGCGCGTTACCTGGTAGCGGCC
```

PROMOTER REGION OF THE CAPS GENE

CATATGGTGCACTCTCTCAGTACAATCTGCTCTGAATGCCGCATAGTTAAGCCAGTATACGGTAC

-35                PROMOTER     -10

CCTCGAGATAAAAAATTTATTTGCTTTCAGGTACAATTCTTGATATAATATTATCATCTAGAT

RBS

AAATAAAAATTTAAGGATCTT ATG GTA CTT GGT AAA CCT CAA ACG .....

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
( A ) LENGTH: 757 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: CDS
( B ) LOCATION: 90..722

( x i ) SEQUENCE DESCRIPTION: SEQ ID NO:1:

```
GGTACCCTCG AGATAAAAAA TTTATTTGCT TTCAGGTACA ATTCTTGATA TAATATTATC                    60

ATCTAGATAA ATAAAAATTT AAGGATCTT ATG GTA CTT GGT AAA CCT CAA ACG                     113
                                   Met Val Leu Gly Lys Pro Gln Thr
                                    1               5

GAT CCT ACT CTC GAA TGG TTC TTG TCT CAT TGC CAC ATT CAT AAG TAC                     161
Asp Pro Thr Leu Glu Trp Phe Leu Ser His Cys His Ile His Lys Tyr
     10                  15                  20

CCA TCC AAG AGC ACG CTT ATT CAC CAG GGT GAA AAA GCG GAA ACG CTG                     209
Pro Ser Lys Ser Thr Leu Ile His Gln Gly Glu Lys Ala Glu Thr Leu
 25                  30                  35                  40

TAC TAC ATC GTT AAA GGC TCT GTG GCA GTG CTG ATC AAA GAC GAA GAG                     257
Tyr Tyr Ile Val Lys Gly Ser Val Ala Val Leu Ile Lys Asp Glu Glu
                 45                  50                  55

GGT AAA GAA ATG ATC CTC TCC TAT CTG AAT CAG GGT GAT TTT ATT GGC                     305
Gly Lys Glu Met Ile Leu Ser Tyr Leu Asn Gln Gly Asp Phe Ile Gly
                 60                  65                  70

GAA CTG GGC CTG TTT GAA GAG GGC CAG GAA CGT AGC GCA TGG GTA CGT                     353
Glu Leu Gly Leu Phe Glu Glu Gly Gln Glu Arg Ser Ala Trp Val Arg
             75                  80                  85

GCG AAA ACC GCC TGT GAA GTG GCT GAA ATT TCG TAC AAA AAA TTT CGC                     401
Ala Lys Thr Ala Cys Glu Val Ala Glu Ile Ser Tyr Lys Lys Phe Arg
         90                  95                 100

CAA TTG ATT CAG GTA AAC CCG GAC ATT CTG ATG CGT TTG TCT GCA CAG                     449
Gln Leu Ile Gln Val Asn Pro Asp Ile Leu Met Arg Leu Ser Ala Gln
105                 110                 115                 120

ATG GCG CGT CGT CTG CAA GTC ACT TCA GAG AAA GTG GGC AAC CTG GCG                     497
Met Ala Arg Arg Leu Gln Val Thr Ser Glu Lys Val Gly Asn Leu Ala
                125                 130                 135

TTC CTC GAC GTG AGC GGC CGC ATT GCA CAG ACT CTG CTG AAT CTG GCA                     545
Phe Leu Asp Val Ser Gly Arg Ile Ala Gln Thr Leu Leu Asn Leu Ala
                140                 145                 150

AAA CAA CCA GAC GCT ATG ACT CAC CCG GAC GGT ATG CAA ATC AAA ATT                     593
Lys Gln Pro Asp Ala Met Thr His Pro Asp Gly Met Gln Ile Lys Ile
             155                 160                 165

ACC CGT CAG GAA ATT GGC CAG ATT GTC GGC TGC AGT CGT CAA ACC GTG                     641
Thr Arg Gln Glu Ile Gly Gln Ile Val Gly Cys Ser Arg Gln Thr Val
         170                 175                 180

GGA CGC ATA CTT AAG ATG CTC GAG GAT CAG AAC CTG ATC TCC GCA CAC                     689
Gly Arg Ile Leu Lys Met Leu Glu Asp Gln Asn Leu Ile Ser Ala His
185                 190                 195                 200

GGT AAA ACC ATC GTC GTT TAC GGC ACT CGT TAA TCCCGTCGGA GTGGCGCGTT                   742
Gly Lys Thr Ile Val Val Tyr Gly Thr Arg *
                205                 210

ACCTGGTAGC GCGCC                                                                     757
```

( 2 ) INFORMATION FOR SEQ ID NO:2:

( i ) SEQUENCE CHARACTERISTICS:
        ( A ) LENGTH: 210 amino acids
        ( B ) TYPE: amino acid
        ( D ) TOPOLOGY: linear     ( i i ) MOLECULE TYPE: protein     ( x i ) SEQUENCE DESCRIPTION: SEQ ID NO:2:

```
Met Val Leu Gly Lys Pro Gln Thr Asp Pro Thr Leu Glu Trp Phe Leu
 1               5                  10                  15

Ser His Cys His Ile His Lys Tyr Pro Ser Lys Ser Thr Leu Ile His
                 20                  25                  30
```

| | | | | | | | | | | | | | | |
|---|---|---|---|---|---|---|---|---|---|---|---|---|---|---|
|Gln|Gly|Glu 35|Lys|Ala|Glu|Thr|Leu 40|Tyr|Tyr|Ile|Val|Lys 45|Gly|Ser|Val|

Ala Val Leu Ile Lys Asp Glu Glu Gly Lys Glu Met Ile Leu Ser Tyr
    50                    55                    60

Leu Asn Gln Gly Asp Phe Ile Gly Glu Leu Gly Leu Phe Glu Glu Gly
65                    70                    75                    80

Gln Glu Arg Ser Ala Trp Val Arg Ala Lys Thr Ala Cys Glu Val Ala
              85                    90                    95

Glu Ile Ser Tyr Lys Lys Phe Arg Gln Leu Ile Gln Val Asn Pro Asp
            100                   105                   110

Ile Leu Met Arg Leu Ser Ala Gln Met Ala Arg Arg Leu Gln Val Thr
          115                   120                   125

Ser Glu Lys Val Gly Asn Leu Ala Phe Leu Asp Val Ser Gly Arg Ile
    130                   135                   140

Ala Gln Thr Leu Leu Asn Leu Ala Lys Gln Pro Asp Ala Met Thr His
145                   150                   155                   160

Pro Asp Gly Met Gln Ile Lys Ile Thr Arg Gln Glu Ile Gly Gln Ile
              165                   170                   175

Val Gly Cys Ser Arg Gln Thr Val Gly Arg Ile Leu Lys Met Leu Glu
            180                   185                   190

Asp Gln Asn Leu Ile Ser Ala His Gly Lys Thr Ile Val Val Tyr Gly
        195                   200                   205

Thr Arg
    210

(2) INFORMATION FOR SEQ ID NO:3:

(i) SEQUENCE CHARACTERISTICS:
        (A) LENGTH: 171 base pairs
        (B) TYPE: nucleic acid
        (C) STRANDEDNESS: single
        (D) TOPOLOGY: linear     (ii) MOLECULE TYPE: DNA (genomic)

(xi) SEQUENCE DESCRIPTION: SEQ ID NO:3:

CATATGGTGC ACTCTCAGTA CAATCTGCTC TGAATGCCGC ATAGTTAAGC CAGTATACGG    60

TACCCTCGAG ATAAAAAATT TATTTGCTTT CAGGTACAAT TCTTGATATA ATATTATCAT  120

CTAGATAAAT AAAAATTTAA GGATCTTATG GTACTTGGTA AACCTCAAAC G         171

(2) INFORMATION FOR SEQ ID NO:4:

(i) SEQUENCE CHARACTERISTICS:
        (A) LENGTH: 23 base pairs
        (B) TYPE: nucleic acid
        (C) STRANDEDNESS: single
        (D) TOPOLOGY: linear     (ii) MOLECULE TYPE: DNA (genomic)

(xi) SEQUENCE DESCRIPTION: SEQ ID NO:4:

GATGAGTTCG TGTCCGTACA ACT                                                  23

(2) INFORMATION FOR SEQ ID NO:5:

(i) SEQUENCE CHARACTERISTICS:
        (A) LENGTH: 23 base pairs
        (B) TYPE: nucleic acid
        (C) STRANDEDNESS: single
        (D) TOPOLOGY: linear ( i i ) MOLECULE TYPE: DNA (genomic)

( x i ) SEQUENCE DESCRIPTION: SEQ ID NO:5:

GGTTATCGAA ATCAGCCACA GCG  23

POSITIVE SELECTION VECTOR BASED ON THE CAPS GENE, PCAPS VECTOR AND ITS USE

DESCRIPTION

The present invention concerns a vector with a positive selection possibility for cloning a DNA sequence in a host cell transformed with the vector, wherein the vector contains suitable restriction cleavage sites within a selection gene the expression of which is prevented by insertion of the foreign gene, a process for the construction of a vector according to the invention as well as the use of the vector as a positive selection vector for cloning DNA sequences and finally processes for cloning DNA sequences by inserting the DNA sequence into a selection gene of a positive selection vector and subsequently replicating the vector in suitable host cells and a kit for cloning DNA sequences.

An isolated DNA fragment is adequate for some applications in molecular biology. In the case of applications such as transcription, mutation, sequencing or expression it is, however, important to obtain a bacterial clone which contains the respective DNA fragment.

When DNA is cloned, the DNA fragments to be cloned are typically produced by cleaving the DNA with a suitable restriction enzyme. The DNA fragments are subsequently ligated with a vector which has been constructed in a suitable manner, ligated and transformed in competent cells.

In cases in which the DNA is DNA amplified by PCR, various cloning strategies can be applied. Hence for example the recognition sequences for a restriction endonuclease can be incorporated at the ends of the respective primer sequences. Thus the end of the DNA fragment generated by PCR carries the corresponding restriction sequence and can be cleaved with the respective restriction enzyme after the PCR (Kaufmann and Evans, 1990, BioTechniques 9, 304–306).

A further cloning strategy is to utilize the so-called extendase activity of DNA polymerases. When for example Taq DNA polymerase is used a non template-dependent extension of the PCR product occurs at the 3' end of the PCR product (Clark, 1989, Nucl. Acids Res. 20, 9677–9686). In this process a single deoxyadenosine monophosphate is preferably attached to the 3' ends of the DNA of some of the PCR products. Taq DNA polymerase (and other DNA polymerases without 3'–5' exonuclease activity) thus generate a PCR product with a DNA end which can be used for a ligation with a suitable vector (each with one thymidine monophosphate at the 3' ends; (Mead et al., 1991, Biotechnol. 9, 657–663; PCT Application WO 92/06189).

Furthermore PCR products can be ligated into a suitable vector by means of a so-called blunt end ligation. This method is preferably used when the respective PCR fragment has been amplified with a polymerase with 3'–5' exonuclease activity (i.e. without extendase activity; Costa et al., 1994, PCR Meth. and Appl. 3, 338–345; Lohff and Cease, 1991, Nucl. Acids Res. 20 (1), 144).

Numerous different vectors are available for cloning DNA into E. coli. A subgroup of these cloning vectors, the so-called positive selection vectors, allow the direct selection of clones which carry a DNA fragment as an insert in the respective vector. In this process the respective DNA fragment is inserted by cloning into a (for example) lethal gene. Bacterial clones which carry a vector whose lethal gene has not been inactivated by insertion of a DNA fragment, express this lethal gene and thus cannot survive. This results in a selection of clones which carry the desired DNA fragment. Vectors with such properties are called suicide vectors. Hence the use of suicide vectors for positive selection is an efficient strategy to suppress an undesired background of non-recombinant clones (and hence false positive clones) which do not carry the desired DNA insert.

Some positive selection vectors are based on the inactivation of the selecting gene by insertion of the DNA fragment to be cloned into the selecting gene. In this case these genes may be lethal genes (Henrich & Plapp, 1986, Gene 42, 345–349; Henrich & Schmidtberger, 1995, Gene 154, 51–54; Bernard et al., 1994, Gene 148, 71–74, PCT Application WO 94/03616). Further principles that have been described are the abolition of a particular sensitivity towards metabolites (Kast, 1994, Gene 138, 109–114), selection by means of DNA-degrading or RNA-degrading enzymes (Yaznin et al., 1996, Gene 169, 131–132; Ahrenholtz et al., 1994, Appl. Environ. Microbiol. 60 (10), 3746–3751) as well as selection by means of unstable long palindromic DNA sequences (Altenbuchner et al., 1992, Methods. Enzymol. 216, 457–466).

When restriction endonucleases are used to cleave vector DNA and/or a DNA fragment there is a limitation in that in this method an undesired cleavage within the sequence of the DNA to be cloned may occur. Consequently only those restriction cleavage sites can be incorporated into the primer which are not present in the respective DNA fragment. Moreover the synthesis of this additional primer sequence is expensive. Furthermore the cleavage efficiency of these restriction cleavage sites located at the ends of the primers is less than that of cleavage sites that are located within a DNA section (Jung et al., 1990, Nucl. Acids Res. 18 (20), 6156). In addition it may be necessary to purify the DNA beforehand and afterwards.

When a vector is used with a thymidine monophosphate overhang (T vector) there is a limitation in that DNA polymerases with a 3'-5' exonuclease activity (so-called proof reading activity) do not produce a PCR product with a 3' overhang of a deoxyadenosine monophosphate. These polymerases produce a blunt end at the 3' end of the PCR product (Hu, 1993, DNA Cell Biol. 12 (8), 763–770). These PCR products cannot be cloned with T vectors. Such polymerases are for example the DNA polymerase from Pyrococcus woesei (Pwo polymerase) or from Pyrococcus furiosus (Pfu polymerase). Hence such polymerases cannot be used in combination with T vectors. There is also a limitation when using mixtures of polymerases which are each composed of at least one polymerase with and one polymerase without 3'-5' activity; in these cases a low cloning efficiency is observed. Moreover it is known that the Taq DNA polymerase (depending on the template sequence) is able to also attach other nucleotides as a deoxyadenosine monophosphate to the 3' end of the PCR product (Hu, 1993, DNA Cell. Biol. 12 (8), 763–770). Such DNA fragments are not suitable for cloning with a T vector.

One of the problems that can arise when using positive selection vectors is a high number of false positive clones i.e. clones without an insert (Henrich & Plapp, 1986; Gene 42, 345–349; Bernhard et al., 1994, Gene, 148, 71–74). This can be caused by a growth of clones whose selection genes are mutated (so called revertants).

Furthermore the use of positive selection vectors may result in a gene product with diminished function but nevertheless functional when cloning short DNA fragments which leads to an occurrence of clones with reduced growth and thus complicates the evaluation of a cloning experiment.

In those cases in which the insertion of DNA fragments does not in any way adversely affect the lethal properties of the selection gene, also no clones with an insert are obtained; i.e. it is not possible to clone the respective DNA fragments. This may occur in particular with small DNA fragments or/and those fragments whose nucleotide sequence is "in frame" with the selection gene.

A further disadvantage for an application is when complex nutrient media have to be used in order to utilize the selection mechanism (Kast, 1994, Gene 138, 109–114).

Therefore the object of the present invention was to create a possibility of carrying out a positive selection when cloning DNA sequences and to avoid the disadvantages of the state of the art. This object is achieved according to the invention by a vector with a positive selection possibility for cloning a DNA sequence into a host cell transformed with the vector, wherein the vector contains suitable restriction cleavage sites within a selection gene the expression of which is prevented by the insertion of the foreign gene, the vector being characterized in that it contains a modified cap gene (=crp gene, CAMP receptor protein gene) as a selection gene which codes for a CAP protein with modified DNA binding specificity whose expression is lethal for adenylate-cyclase-positive host cells. As a rule all E. coli strains are adenylate-cyclase-positive and are thus suitable for an application of the vector according to the invention. The vectors according to the invention are suitable for being used to clone DNA fragments in general and in particular DNA fragments which are produced by the PCR method.

A distinguishing feature of the vectors according to the invention is that they have a form of the cap gene modified by mutation as a positive selection principle which codes for a modified form of the Catabolite Activator Protein (CAP). The CAP protein is a prokaryotic transcription factor which is involved in the regulation of carbohydrate metabolism. The function of the CAP protein is well described particularly for E. coli. cAMP is necessary for its function (Zubay et al., 1970, PNAS 66 (1), 104–110). In a particularly preferred embodiment the vector according to the invention carries a modification of the cap gene at a site which, after expression, results in a mutant which contains an amino acid substitution at position 181 of the protein. In a particularly preferred embodiment the mutant CAPs contains glutamine instead of glutamic acid at position 181. This mutation relaxes the binding specificity for DNA and extends the DNA binding potential. Bacterial clones that are transformed with a vector according to the invention cannot survive since the expression of the mutated cap gene is lethal for these clones. The modified cap gene can only be cloned in adenylate-cyclase-negative strains (cya$^-$). When cAMP is present the modified CAP protein is lethal for bacteria due to binding to sequences which are not yet known in detail and can therefore be used for a suicide cloning vector.

All forms of the cap gene modified by mutation can be used for such an application provided they code for modified CAP proteins which also have the desired modified DNA binding properties and hence possess lethal properties for adenylate-cyclase-positive host strains.

Advantages of the vector system according to the invention are in particular the high proportion of positive clones (which contain the expected DNA insert) that were obtained in the cloning experiments. Furthermore when cloning short DNA fragments and those DNA fragments which are present "in frame" with the selection gene, the lethal properties of the mutated cap gene are abolished i.e. such DNA fragments can be cloned when using the mutated CAP system. In addition when using the mutated CAP system no special experimental methods such as e.g. primer design, induction (temperature shifts, IPTG) or special media compositions (X-Gal, complex nutrient media) are required. The vectors according to the invention are suitable for cloning DNA fragments by means of ligation via overhanging ends as well as via blunt ends (sticky end and blunt end ligation). The vector pCAPs which is particularly preferred according to the invention is especially suitable for this.

A further subject matter of the present invention is a process for the production of a vector according to the invention in which a vector containing the cap gene is modified within the cap gene in such a way that a vector according to the invention with an appropriately modified cap gene is formed or an already modified cap gene is inserted into a suitable vector, wherein in both cases the vectors obtained are cloned into adenylate-cyclase-negative host cells.

In the process according to the invention the cap gene is preferably modified at a site which leads to an amino acid substitution of amino acid 181 of the CAP protein. In a particularly preferred embodiment glutamic acid is replaced by glutamine in this process. In addition it is particularly preferable to insert a strong promoter in front of the cap gene.

A further subject matter of the present invention is the use of a vector according to the invention as a positive selection vector for cloning DNA sequences in which the DNA sequence is inserted into the vector within the modified cap gene and adenylate-cyclase-positive host cells are used for cloning.

A process for cloning DNA sequences by inserting the DNA sequence into a selection gene of a positive selection vector and subsequently replicating the vector in suitable host cells is also a subject matter of the invention. In this case one uses a vector according to the invention as the selection vector, inserts the DNA sequence to be cloned into a suitable restriction cleavage site within the modified cap gene and carries out the cloning in adenylate-cyclase-positive host cells. The insertion of the DNA sequence into the modified cap gene prevents formation of the modified CAP protein. However, the modified cap gene would prevent cloning in adenylate-cyclase-positive host cells since it has lethal effects on the host cells and these would therefore die. However, due to the insertion of the DNA sequence, the CAP protein is no longer expressed in a functional form which is why the cloning can also take place in adenylate-cyclase-positive host cells. Hence according to the invention the formation of false positive clones is avoided since these false positive clones would kill the host cell.

The process according to the invention is particularly preferably used for DNA sequences which have been produced by the PCR technique. Clones are preferably obtained with the aid of the process according to the invention which contain the desired DNA sequence. In addition reference is made to the advantages already mentioned above of the vector system according to the invention and the use thereof.

A further subject matter of the present invention is a reagent kit for the selective cloning of DNA sequences containing a) a vector according to the invention as well as b) adenylate-cyclase-positive host cells.

The reagent kit according to the invention enables DNA sequences to be cloned with the aid of the system and process according to the invention. In this process DNA sequences obtained by PCR are particularly preferably cloned.

In a particularly preferred embodiment of the invention the reagent kit additionally contains suitable restriction endonucleases for inserting the DNA sequence into the selection gene of the vector according to the invention.

The following examples elucidate the invention in more detail in conjunction with the figures.

EXAMPLE 1

Vector Construction

Figure 1:
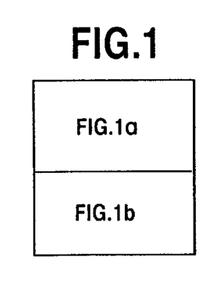
FIG. 1 shows the DNA sequence [SEQ ID NO. 1] and amino acid [SEQ ID NO. 2] sequence of the mutated cap gene.
Figure 1A:
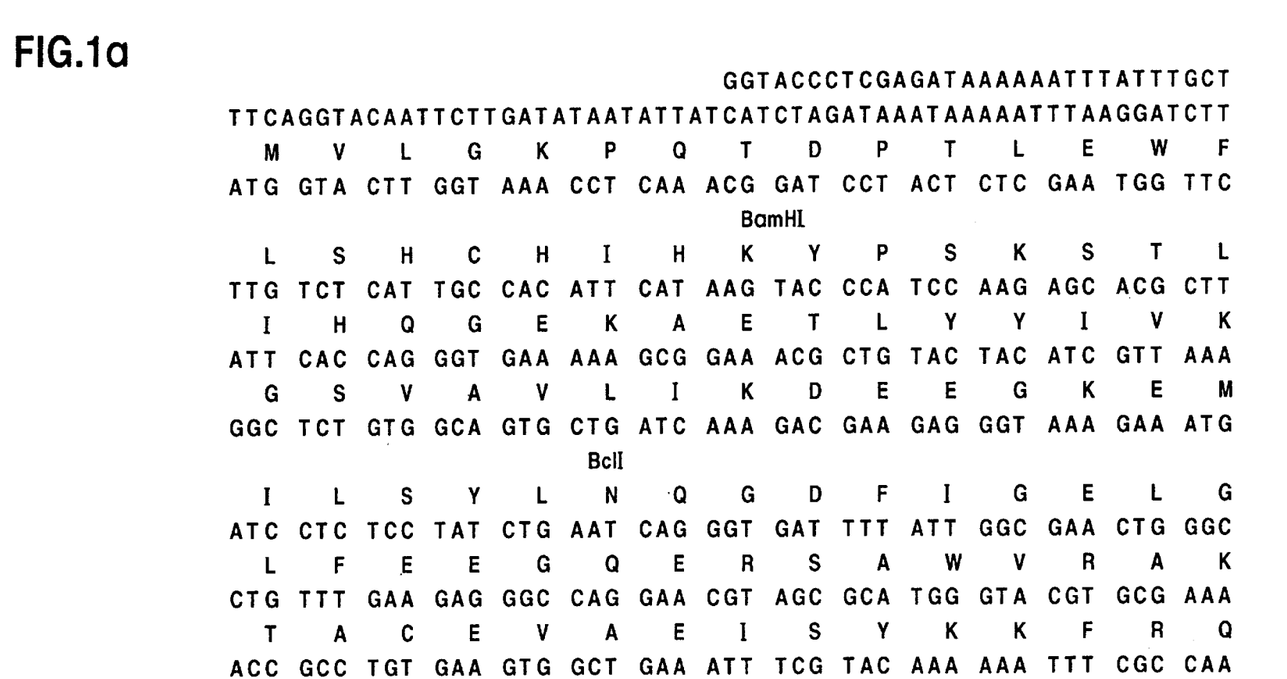
Figure 1B:
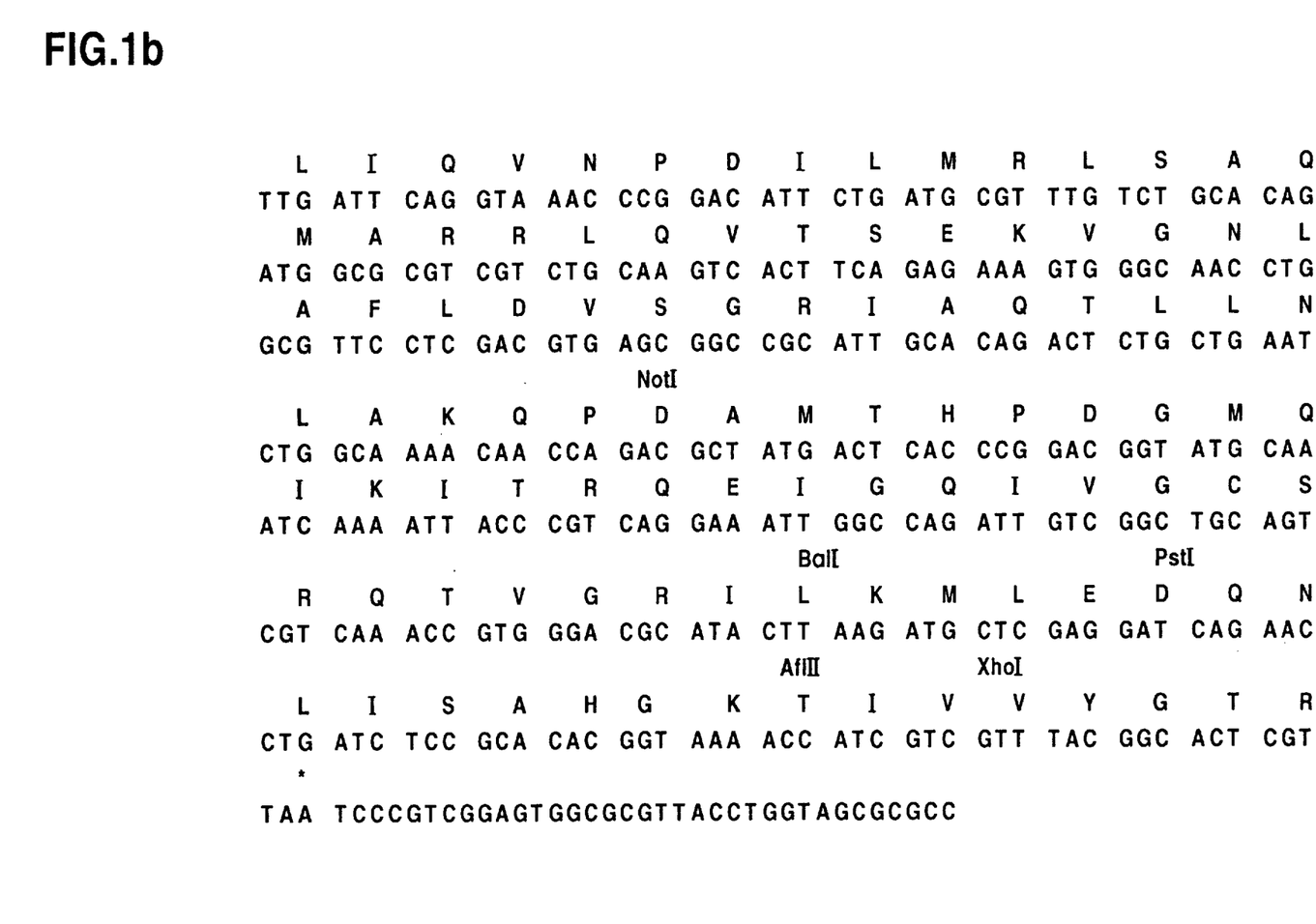
Figure 2:
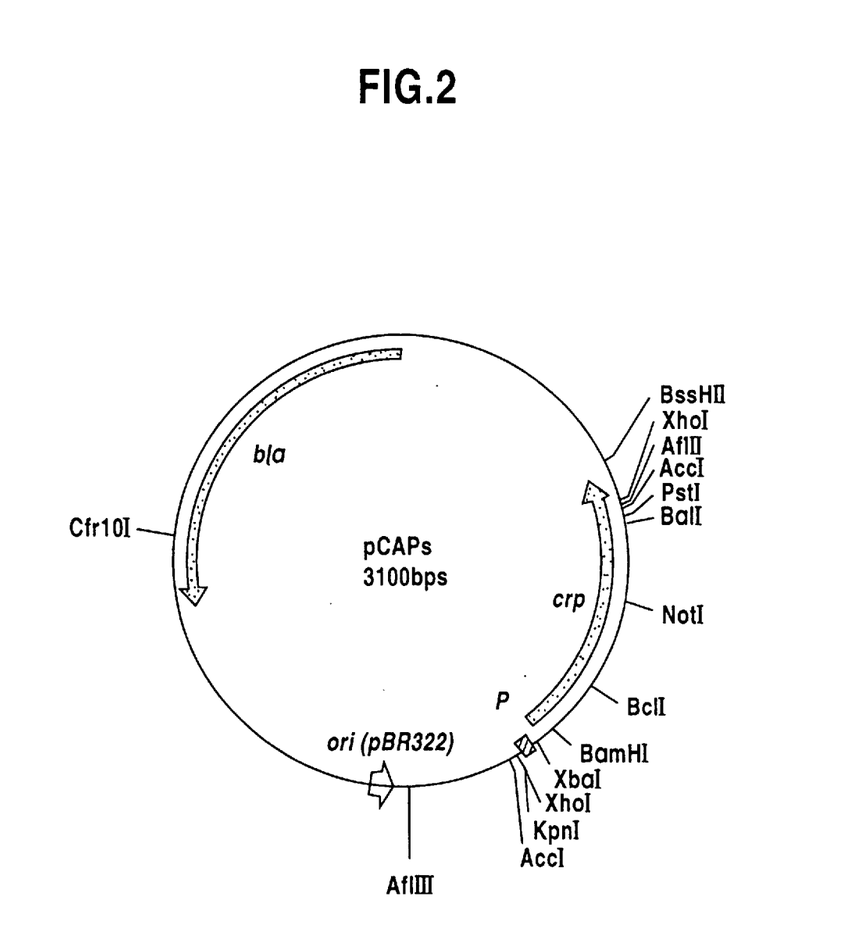
FIG. 2 shows a schematic representation of the vector pCAPs [SEQ ID NO. 3]
Figure 3:
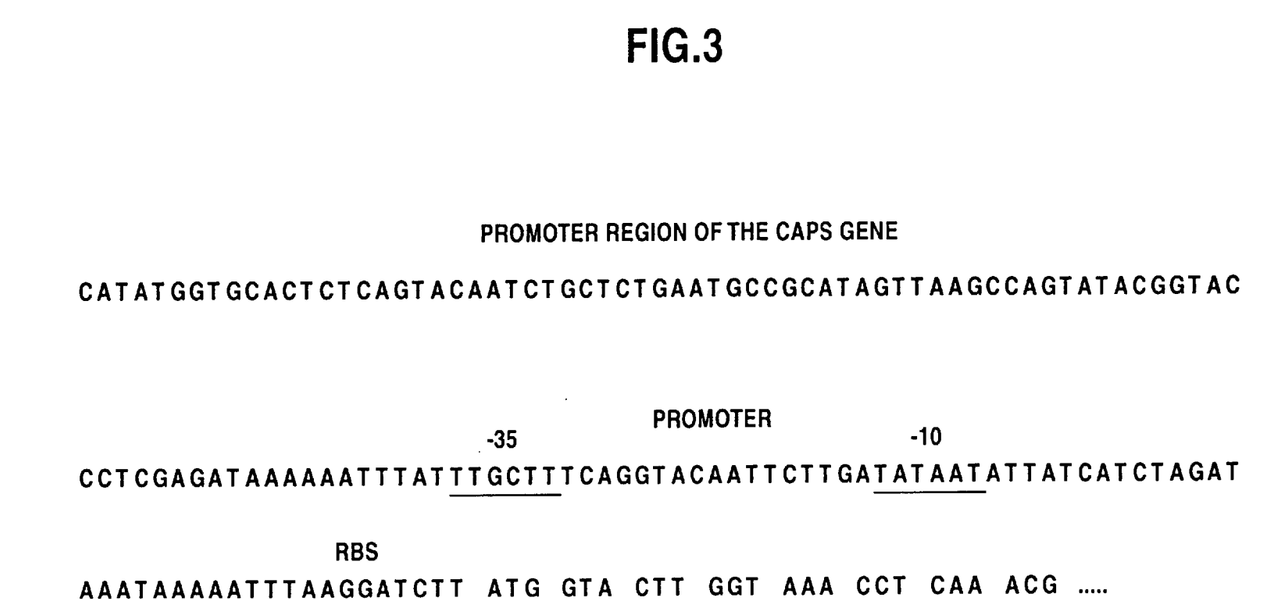
FIG. 3 shows the promoter sequences of pCAPs.

The cap gene was cleaved from the vector pHA7 using EcoRV/HindIII (Aiba et al., 1982, Nucl. Acids Res. 10, 1345) and subsequently cloned into the vector pEE4/StuI/HindIII. The cap gene was cleaved from this vector pEE4-CAP by means of EcoRI/HindIII and cloned into pUC19/EcoRVHindIII. Subsequently the cap gene was cloned behind the synthetic promoter of the vector pWB100 (Lehming et al., 1987, EMBO J. 6, 3345–3353). For this pUC 19-CAP was linearized with HindIII, the overhanging 5' single strand ends were filled in with a Klenow fragment of DNA polymerase I, digested with CfrI, the fragment was purified and cloned into the vector pWB100 cleaved with CfrI/EcoRV. This yields the vector pBG1. This vector was further modified by cloning in a stronger promoter sequence derived from the piWiT10 promoter. The vector obtained is pCAP. The vector pCAPs was obtained by mutation of the cap gene at amino acid position 181 (glutamic acid into glutamine).

EXAMPLE 2

Cloning of DNA Fragments

General methods:

The production of competent *E. coli* cells (e.g. *E. coli* JM83, XL1-Blue, DH5α, BMH8117) for the transformation as well as the transformation of the cells was carried out according to standard methods (Hanahan, 1983, J. Mol. Biol. 166, 557–580). Commercially available competent cells such as *E. coli* XL1-Blue MRF' kan, Stratagene were also used for the cloning. The cells were plated out on LB medium containing ampicillin (100–200 μg/ml).

The cleavage of DNA (vector or DNA fragment) with restriction endonucleases was carried out according to the instructions of the respective manufacturer.

The ligation of linearized vector and DNA fragment was carried out according to standard methods (Maniatis et al. 1982, Molecular cloning. A laboratory manual, Cold Spring Harbour Laboratory Press, Cold Spring Harbour, N.Y.). A commercially available kit was also used for this (e.g. rapid ligation kit, Boehringer Mannheim).

The amplifications of DNA by means of PCR was carried out with the appropriate DNA polymerases according to the manufacturer's instructions.

Example of blunt end cloning:

The vector pCAPs is linearized by digestion with the restriction enzyme BalI according to the manufacturer's instructions. This linearized plasmid (5 ng) is ligated with a 0.25 kb long isolated StuI fragment of the vector piWiT10WL1 (von Wilcken-Bergmann et al., 1986, EMBO J. 5 (12), 3219–3225) in a 10-fold molar excess. Subsequently competent cells of *E. coli* DH5α are transformed with this, plated out on LB medium and incubated overnight at 370° C. In each case 5 ml cultures are set-up from the clones obtained, grown overnight and plasmid preparations of these are prepared. Restriction cleavages with the enzymes XbaI/SphI are carried out to identify the plasmids. In the example described here the analysis of 102 examined clones yielded a number of 92 clones with the insert.

Example of sticky end cloning:

The vector pCAPs is linearized by digestion with the restriction enzyme PstI according to the manufacturer's instructions. This linearized plasmid (5 ng) is ligated with a 0.25 kb long isolated PstI fragment of the vector piWiT10WLI (von Wilcken-Bergmann et al., 1986, EMBO J. 5 (12), 3219–3225) in a 10-fold excess. Subsequently competent cells of *E. coli* DH5α are transformed with this, plated out on LB medium and incubated overnight at 37° C. In each case 5 ml cultures are set-up from the clones obtained, grown overnight and plasmid preparations of these are prepared. Restriction cleavages with the enzymes XbaI/StuI are carried out to identify the plasmids. In the example described here the analysis of 108 examined clones by agarose gel electrophoresis yielded a number of 100 clones with the insert.

Example of cloning PCR products:

The PCR products were produced by amplifying a 0.5 kb fragment from lambda DNA. Various polymerases and mixtures thereof were used for the amplification. In this case a polymerase without 3'–5' exonuclease activity (Taq DNA polymerase), a polymerase with 3'–5' exonuclease activity (Pwo DNA polymerase) as well as a mixture of these two polymerases (Expand High Fidelity PCR System) were used.

The primers used for the PCR have the following sequences:

Forward primer: 5'-GAT GAG TTC GTG TCC GTA CAA CT-3 [SEQ ID NO. 4]

Reverse primer: 5'-GGT TAT CGA AAT CAG CCA CAG CG-3 [SEQ ID NO. 5]

The PCR conditions were:

1 ng lambda DNA

20 μM primer (forward, reverse)

0.2 mM dNTPs

10 μl PCR buffer (suitable for the respectively used polymerases)

The following polymerases were used in each case:

2.5 units Taq DNA polymerase 2.5 units Pwo DNA polymerase 1.75 units Expand High Fidelity PCR System filled up to 100 μl with redistilled water.

The cycle conditions were as follows:

2 min at 95° C.; 25 cycles with: 1 min at 94° C., 1 min at 50° C., 3 min at 72° C.; 4 min at 72° C.

The PCR fragments were purified after amplification (High Pure PCR Product Purification Kit, Boehringer Mannheim).

0.1–10 ng vector (linearized with BalI) and typically 1 ng was used for the ligation. 10–500 ng of the purified PCR fragment was used and 100–400 ng in typical experiments. The ligation was carried out according to the protocol of the Rapid Ligation Kit. ¹⁄₁₀ vol of the ligation preparation (0.1 ng vector) was used for the subsequent transformation. 40 μl of the competent cells (*E. coli* XL1-Blue MRF kan) was used according to the manufacturer's instructions (total volume 400 μl). 100 μl of the transformed cells was plated out on LB plates (ampicillin, 100 μg/ml) and incubated overnight at 37° C. The clones obtained were cultured overnight at 37° C. in LB medium (ampicillin 150 μg/ml). The plasmid DNA was isolated by standard methods (Maniatis et al. 1982, Molecular Cloning. A laboratory manual, Cold Spring Harbour Laboratory Press, Cold Spring Harbour, N.Y.). The isolated plasmids were analysed by restriction cleavage with AccI. The result of a typical experiment is shown in table 1:

TABLE 1

| pCAPs (vector in ligation) | PCR fragment (polym. used) | colonies/plate | pos. clones/ analysed clones |
|---|---|---|---|
| 1 ng | 400 ng (Taq DNA pol.) | 2 | 2/2 |
| 1 ng | 100 ng (Taq DNA pol.) | 4 | 3/4 |
| 1 ng | 400 ng (Pwo DNA pol.) | 62 | 18/18 |
| 1 ng | 100 ng (Pwo DNA pol.) | 193 | 48/48 |
| 1 ng | 400 ng (Epand High Fid.) | 9 | 9/9 |
| 1 ng | 100 ng (Epand High Fid.) | 10 | 7/10 |

The vector pCAPs is particularly suitable for the blunt end cloning of PCR fragments (which have for example been produced by means of Pwo DNA polymerase) due to the high number of clones obtained as well as the high proportion of positive clones (100% in the example shown).

A high proportion of positive clones is obtained when PCR fragments are cloned which have been produced using a mixture of polymerases (Expand High Fidelity PCR System) if a high insert/vector ratio is present in the ligation reaction.

When cloning PCR fragments which have been produced using Taq DNA polymerase it is also possible to obtain a number of clones even though this number is less. In this case those PCR products of the Taq DNA polymerase are ligated which have no A overhang.

In this connection it is known that the efficiency of the cloning of PCR fragments which have been produced using Taq DNA polymerase can be improved by a subsequent so-called polishing of the PCR products (a degradation of the A overhang by the 3'–5' exonuclease activity of polymerases; Costa & Weiner, 1994, Nucl. Acids Res. 22 (12), 2423).

EXAMPLE 3

Example of the Cloning of Non-Purified PCR Products

In addition to cloning purified PCR products, non-purified PCR products were also cloned i.e. an aliquot of the PCR mixture was used directly in the ligation reaction. For this blunt end PCR products were produced using Pwo DNA polymerase by amplifying a 0.5 kb fragment from lambda DNA.

The primers used for the PCR have the following sequences:
Forward primer: 5'-GAT GAG TTC GTG TCC GTA CAA CT-3'[SEQ ID NO. 4])
Reverse primer: 5'-GGT TAT CGA AAT CAG CCA CAG CG-3'[SEQ ID NO. 5])
The PCR conditions were:
1 ng lambda DNA
20 µM primer (forward, reverse)
0.2 mM dNTPs
10 µl PCR buffer (suitable for Pwo DNA polymerase)
2.5 units Pwo DNA polymerase
Filled up to 100 µl with redistilled water.

The cycle conditions were as follows: 2 min at 95° C.; 25 cycles with: 1 min at 94° C., 1 min at 50° C., 3 min at 72° C., 4 min at 72° C.

The subsequent ligation was carried out according to the protocol of the Rapid Ligation Kit (Boehringer Mannheim, order No. 1635-379). 0.1–10 ng vector (linearized with Mlu NI) and typically 1 ng was used for the ligation. The PCR fragments were used unpurified for the ligation after amplification. 1–5 µl of the PCR mixture were used for the ligation (typically 1 µl). 1/10 vol of the ligation preparation (0.1 ng vector) was used for the subsequent transformation. 40 µl of the competent cells (*E. coli* XL1-Blue MRF' kan, Stratagene) was used according to the manufacturer's instructions (total volume 400 µl). 100 µl of the transformed cells was plated out on LB plates (ampicillin, 100 µg/ml) and incubated overnight at 37° C. The clones obtained were cultured overnight at 37° C. in LB medium (ampicillin 150 µg/ml). The plasmid DNA was isolated by standard methods (Maniatis et al. 1982, Molecular Cloning. A laboratory manual, Cold Spring Harbour Laboratory Press, Cold Spring Harbour, N.Y.). The isolated plasmids were analysed by restriction cleavage with AccI and subsequent agarose gel electrophoresis. In this case>95% of the analysed clones (92 of 96) showed the 0.5 kb PCR fragment as an insert.

We claim:

1. A vector for cloning a DNA sequence into adenylate-cyclase-positive host cells, the vector containing a selection gene comprising a modified cap gene which codes for a modified CAP protein with reduced DNA binding specificity compared with a wild-type CAP protein, the expression of which selection gene is lethal in a portion of the host cells, wherein a restriction site for the DNA sequence is located within the selection gene and upon insertion of the DNA sequence at the restriction site, the expression of the selection gene in the host cells is prevented, wherein the modified cap gene is modified such that the glutamic acid at position 181 of the wild-type CAP protein is substituted by glutamine.

2. The vector as claimed in claim 1, further containing a promoter upstream of the selection gene.

3. The vector pCAPs.

4. A process for producing a vector for cloning a DNA sequence into adenylate-cyclase-positive host cells, the process comprising providing a vector;

providing in the vector a selection gene comprising a modified cap gene, the providing step comprising modifying the cap gene within the vector or inserting a modified cap gene into the vector, wherein the modified cap gene codes for a modified CAP protein with reduced DNA binding specificity compared with a wild-type CAP protein, and the expression of the modified cap gene is lethal in a portion of the host cells, wherein a restriction site for the DNA sequence is located within the selection gene and upon insertion of the DNA sequence at the restriction site, the expression of the selection gene in the host cells is prevented, wherein the modified cap gene is modified such that the glutamic acid at position 181 of the wild-type CAP protein is substituted by another amino acid; and replicating or expressing the modified cap gene in adenylate-cyclase-negative host cells.

5. The process as claimed in claim 4, wherein glutamic acid at position 181 of the wild-type CAP protein is substituted by glutamine.

6. The process as claimed in claim 4, wherein a strong promoter is inserted upstream of the selection gene.

7. A process for cloning a DNA sequence into adenylate-cyclase-positive host cells, the process comprising providing a vector containing a selection gene comprising a modified cap gene which codes for a modified CAP protein with reduced DNA binding specificity compared with a wild-type CAP protein, the expression of which selection gene is lethal in a portion of the host cells, wherein a restriction site for the DNA sequence is located within the selection gene and upon insertion of the DNA sequence at the restriction site, the expression of the selection gene in the host cells is prevented, wherein the modified cap gene is modified such that the glutamic acid at position 181 of the wild-type CAP protein is substituted by another amino acid;

inserting the DNA sequence at the restriction site of the vector, thereby preventing the expression of the selection gene in the host cells; and thereafter cloning the vector into the host cells.

8. The process as claimed in claim 7, wherein the DNA sequence is produced by PCR.

9. A kit for cloning a DNA sequence into adenylate-cyclase-positive host cells, comprising a vector containing a selection gene comprising a modified cap gene which codes for a modified CAP protein with reduced DNA binding specificity compared with a wild-type CAP protein, the expression of which selection gene is lethal in a portion of the host cells, wherein a restriction site for the DNA sequence is located within the selection gene and upon insertion of the DNA sequence at the restriction site, the expression of the selection gene in the host cells is prevented, wherein the modified cap gene is modified such that the glutamic acid at position 181 of the wild-type CAP protein is substituted by another amino acid; and adenylate-cyclase-positive host cells.

10. The kit as claimed in claim 9, further comprising a restriction endonuclease for inserting the DNA sequence at the restriction site of the vector.

* * * * *